United States Patent [19]

Palencia Adrubau et al.

[11] Patent Number: 5,075,512
[45] Date of Patent: Dec. 24, 1991

[54] PROCESS FOR PURIFYING TECHNICAL GRADE 1,1-BIS(CHLOROPHENYL)-2,2,2-TRICHLOROETHANOL

[75] Inventors: Jaime Palencia Adrubau; Jaume Castellà Solá, both of Badalona, Spain

[73] Assignee: Sociedad Espanola de Desarrollos Quimicos S.A., Barcelona, Spain

[21] Appl. No.: 618,635

[22] Filed: Nov. 27, 1990

Related U.S. Application Data

[63] Continuation of Ser. No. 448,700, Feb. 11, 1989, abandoned.

[30] Foreign Application Priority Data

Dec. 16, 1988 [ES] Spain ................................. 8803818

[51] Int. Cl.$^5$ ............................................. C07C 29/74
[52] U.S. Cl. .................................... 568/810; 568/812
[58] Field of Search ............... 568/810, 812, 841, 854

[56] References Cited

U.S. PATENT DOCUMENTS 4,705,902 11/1987 Nichols et al. ...................... 568/810

FOREIGN PATENT DOCUMENTS 685133 12/1952 United Kingdom ................ 568/810

Primary Examiner—Werren B. Lone
Attorney, Agent, or Firm—Burns, Doane, Swecker & Mathis

[57] ABSTRACT

A process for purifying technical grade 1,1-bis(chlorophenyl)-2,2,2-trichloroethanol for reducing its content of DDT related impurities, based on dissolving technical grade dicofol in a mixture of water and a first compound selected from the group formed by ethylene glycol monomethyl ether, acetonitrile, hydroxyacetone or dimethyl sulfoxide, to obtain a solution which is extracted with n-decane, separating the resulting phases. The dicofol extracted with the n-decane is recovered by reextraction of the n-decane phase with mixtures of said first compound and water and the purified dicofol is recovered from the polar phase.

12 Claims, 10 Drawing Sheets

PROCESS FOR PURIFYING TECHNICAL GRADE 1,1-BIS(CHLOROPHENYL)-2,2,2-TRICHLOROETHANOL

This application is a continuation, of application Ser. No. 07/448,700, filed Dec. 11, 1989.

BACKGROUND OF THE INVENTION

1. Field of the Invention

The present invention relates to a process for purifying technical grade 1,1-bis(chlorophenyl)-2,2,2-trichloroethanol, commonly known as technical grade dicofol, for reducing its content of impurities related with DDT (DDT.R), to levels even below 0.1% by liquid-liquid extraction using highly selective solvents.

Dicofol is a widely used acaricide for agricultural purposes on cotton and fruit, citrus fruits in particular.

2. Reference to the Prior Art

The preparation of this product is described in U.S. Pat. No. 2,812,280 (Nov. 1957), U.S. Pat. No. 2,812,362 (Nov. 1957) and GB 831,421 (Mar. 1960).

The process initially used consisted of photochemical chlorination (scheme A) of technical grade DDT, a mixture of various products, the main components of which, however, are 1,1-bis(4-chlorophenyl)-2,2,2-trichloroethane (p,p'-DDT, approx. 75% by weight) and 1-(4-chlorophenyl)-1-(2-chlorophenyl)-2,2,2-trichloroethane (o,p'-DDT, approx. 20% by weight), by insertion of chlorine gas in the DDT at melting point.

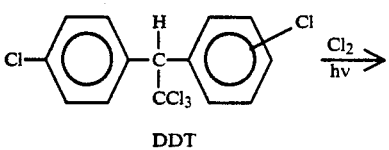

DDT

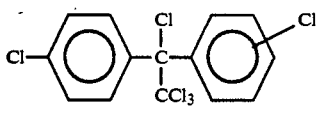

ClDDT (A)

which led to the corresponding chlorine derivatives 1,1-bis-(4-chlorophenyl)-1,2,2,2-tetrachloroethane (p,p'-ClDDT) and 1-(4-chlorophenyl)-1-(2-chlorophenyl)-1,2,2,2,-tetrachloroethane (o,p'-ClDDT).

Because of steric hinderance, the chlorination of the isomer o,p'-DDT is incomplete, there remaining a residue of this substance which represented a content of about 2 to 7% by weight in the final chlorinated product.

The mixture resulting from the chlorination was subsequently submitted to hydrolysis in an acid medium (scheme B), consisting of heating to between 120° and 150° C. with an aqueous solution of sulphuric acid with an arylsulphonic acid.

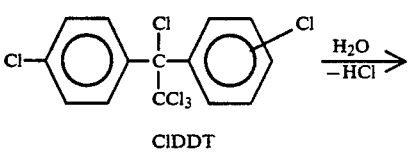

ClDDT

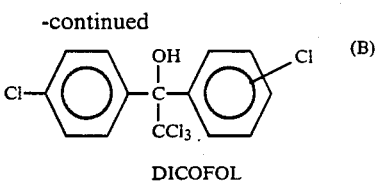

DICOFOL

The dicofol was extracted by dissolution in a solvent and decantation, the organic phase was washed with water and the dicofol was recovered by distillation of the solvent.

The o,p'-DDT was not affected by the hydrolysis and therefore the content thereof in the final technical grade dicofol was about 2 to 6%.

To reduce this content, the manufacturing process was modified by replacing the chlorination by substitution of the DDT with dehydrochlorination first (scheme C), with a strong alkali, to the corresponding ethylene derivatives, 1,1-bis-(4-chlorophenyl)-2,2-dichloroethylene, (p.p'-DDE) and 1-(4-chlorophenyl)-2,2-dichloroethylene (o,p'-DDE),

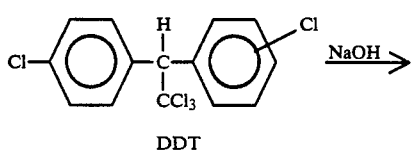

DDT

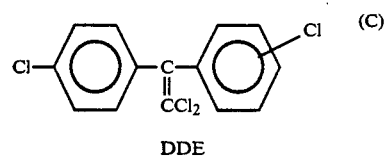

DDE followed by chlorination by addition (scheme D), which is also photochemical, to attain the same chlorinated derivative as in the previous case

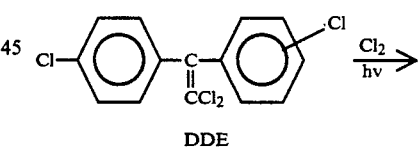

DDE

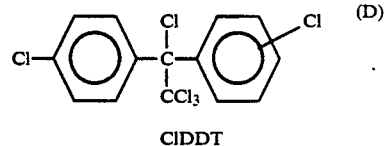

ClDDT which was subjected to the same acid hydrolysis.

Nevertheless, the dicofol prepared by any of these processes contains a number of impurities related with DDT, called DDT.R, the nature of the following being known:

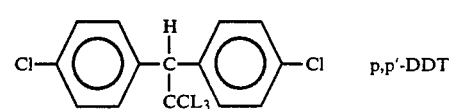  p,p'-DDT

-continued

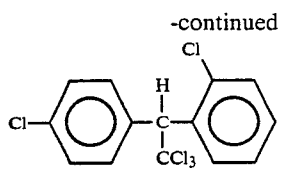 o,p'-DDT

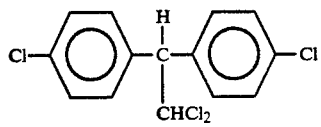 p,p'-DDD

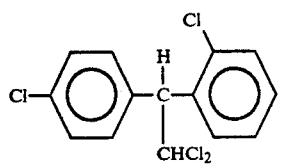 o,p'-DDD

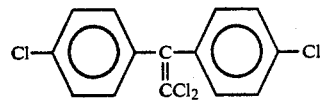 p,p'-DDE

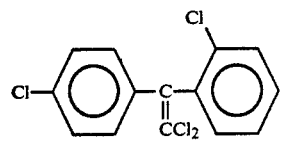 o,p'-DDE

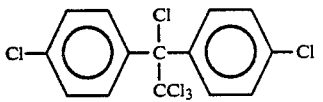 p,p'-ClDDT

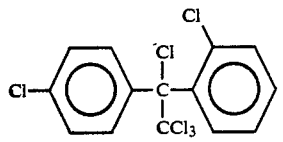 o,p'ClDDT

Other impurities of a known nature contained in dicofol and not considered to be DDT.R, are 4,4'-dichlorobenzophenone (p,p'-DCBF), 2,4'-dichlorpbenzophenone (o,p'-DCBF), 4,4'-dichlorobenzyl (p,p'-DCBZ) and 2,4'-dichlorobenzyl (o,p'-DCBZ).

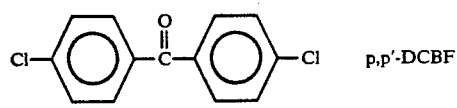 p,p'-DCBF

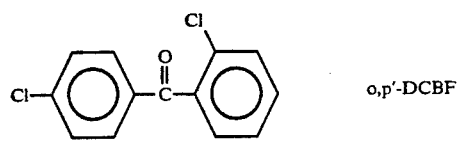 o,p'-DCBF

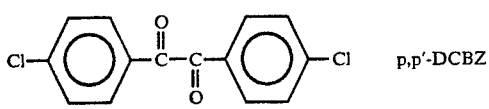 p,p'-DCBZ

-continued

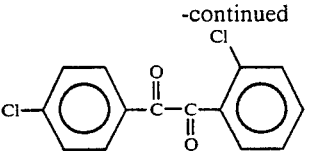 o,p'-DCBZ

As a consequence of the appearance of new specifications (Environmental Protection Agency, Federal Register, 29.05.1986), the DDT.R content of dicofol had to be reduced to 0.1% (by weight) as from 01.01.1989, which means that, for sale in the U.S. this product has to be purified.

U.S. Pat. No. 4,705,902 (November 1987) discloses a process for the purification of technical grade dicofol by liquid-liquid extraction (6,7,8,9) of the DDT.R down to a residual content below 0.1% (by weight). The only two Examples contained therein are: a simulation test of continuous extraction in a counterflowing column with four extraction stages and two recovery stages; and the other as a pilot assay in Karr column (25 mm diam). In both cases it is a question of extracting solutions of dicofol in methanol 90% in water with n-heptane, at an overall concentration lying between 20 and 30%, at atmoshperic pressure and room temperature (23° to 35° C.).

SUMMARY OF THE INVENTION

After a close study, further solvent systems have been found which are more highly selective in the liquid-liquid extraction of the DDT.R from technical grade dicofol, allowing the desired content of 0.1% (by weight) to be attained with a smaller number of steps or a lower DDT.R content and a higher recovery yield to be obtained with the same number of steps.

This object is attained with the process of the invention, which comprises the following steps: a) dissolving the technical grade dicofol in a polar solvent formed by a mixture of water and a first compound selected from the group formed by ethylene glycol monomethyl ether, acetonitrile, hydroxyacetone and dimethylsulfoxide, the water content in the solvent being at the most 25% by weight, giving a solution in which the technical grade dicofol concentration lies between 5 and 35 wt %; b) extracting this solution with n-decane; c) separating the resulting phases; d) recovering the dicofol extracted by the n-decane by reextraction of the n-decane phase with mixtures of said first compound and water; e) recovering the purified dicofol from the polar phase.

The extraction is preferably continuous and the resulting phase are separated by decantation.

According to the invention, when the said first compound is ethylene glycol monomethyl ether, acetonitrile or hydroxyacetone, the dicofol is recovered by distillation of the polar phase at reduced pressure, whereby the mixture of water with ethylene glycol monomethyl ether, with acetonitrile or with hydroxyacetone is recovered and recycled in the process and the 1,1-bis(chlorophenyl)-2,2,2-trichloroethanol, or purified dicofol, is obtained as a residue.

Alternatively according to the invention, when the first compound is dimethyl sulfoxide, the dicofol is recovered by: diluting the dimethyl sulfoxide phase with water; extracting with a second solvent; separating the liquid phases formed; removing said second solvent by reduced pressure distillation, whereby it is recycled to the process, obtaining the purified 1,1-bis(chlorophenyl)-2,2,2-trichloroethanol, or purified dicofol. The dimethyl sulfoxide is preferably recovered from one of the liquid phases formed by distillation and is recycled to the process.

Said second solvent is preferably carbon tetrachloride.

The invention contemplates that the process be conducted preferably continuously at temperatures ranging from 0° to 100° C., either in at least one counterflow column or in mixer-settlers.

BRIEF EXPLANATION OF THE DRAWINGS

Some non-limiting examples of the process of the invention are given hereinafter. Reference is made in said examples to the accompanying drawings. The drawings show.

Figure 3:
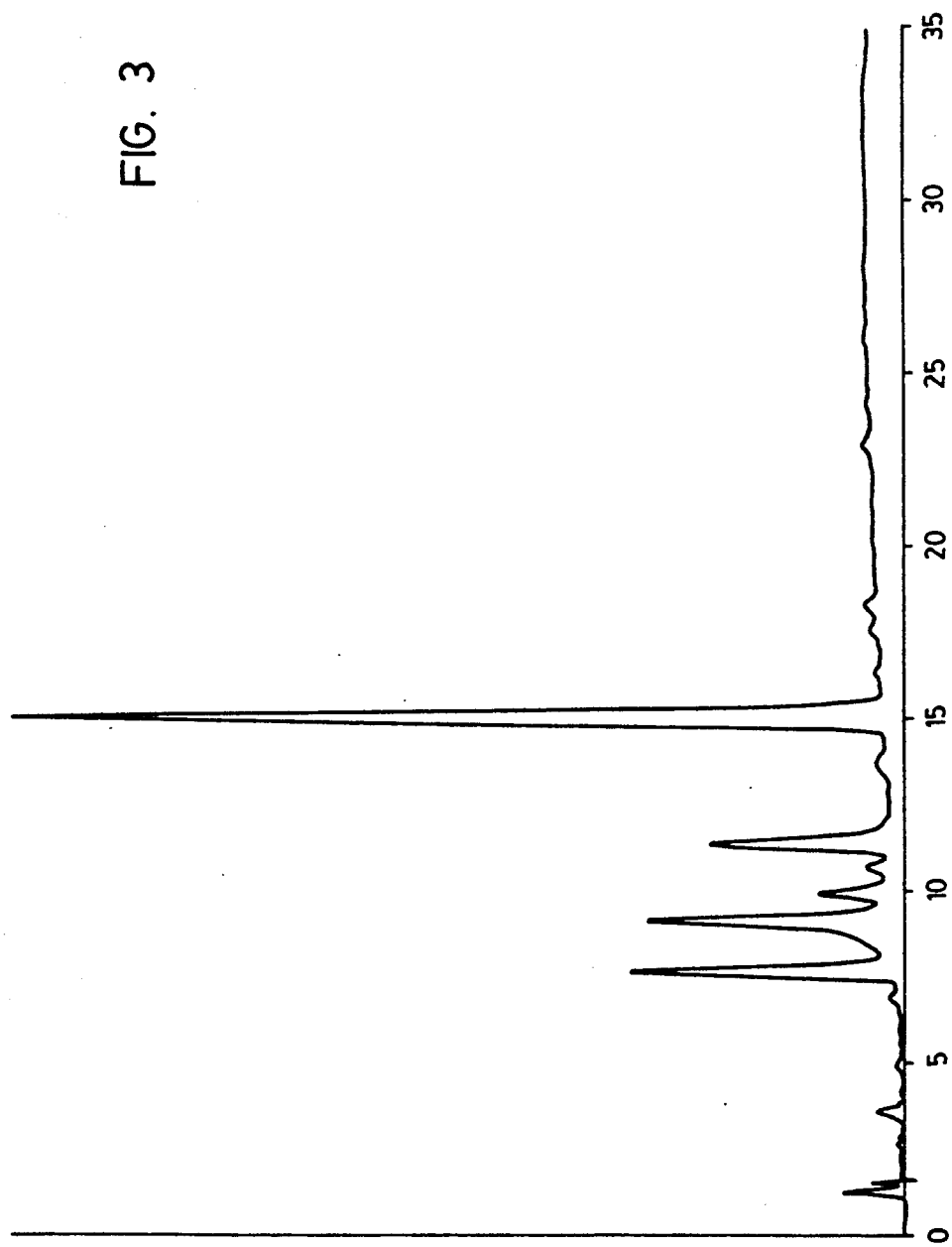
Figure 4:
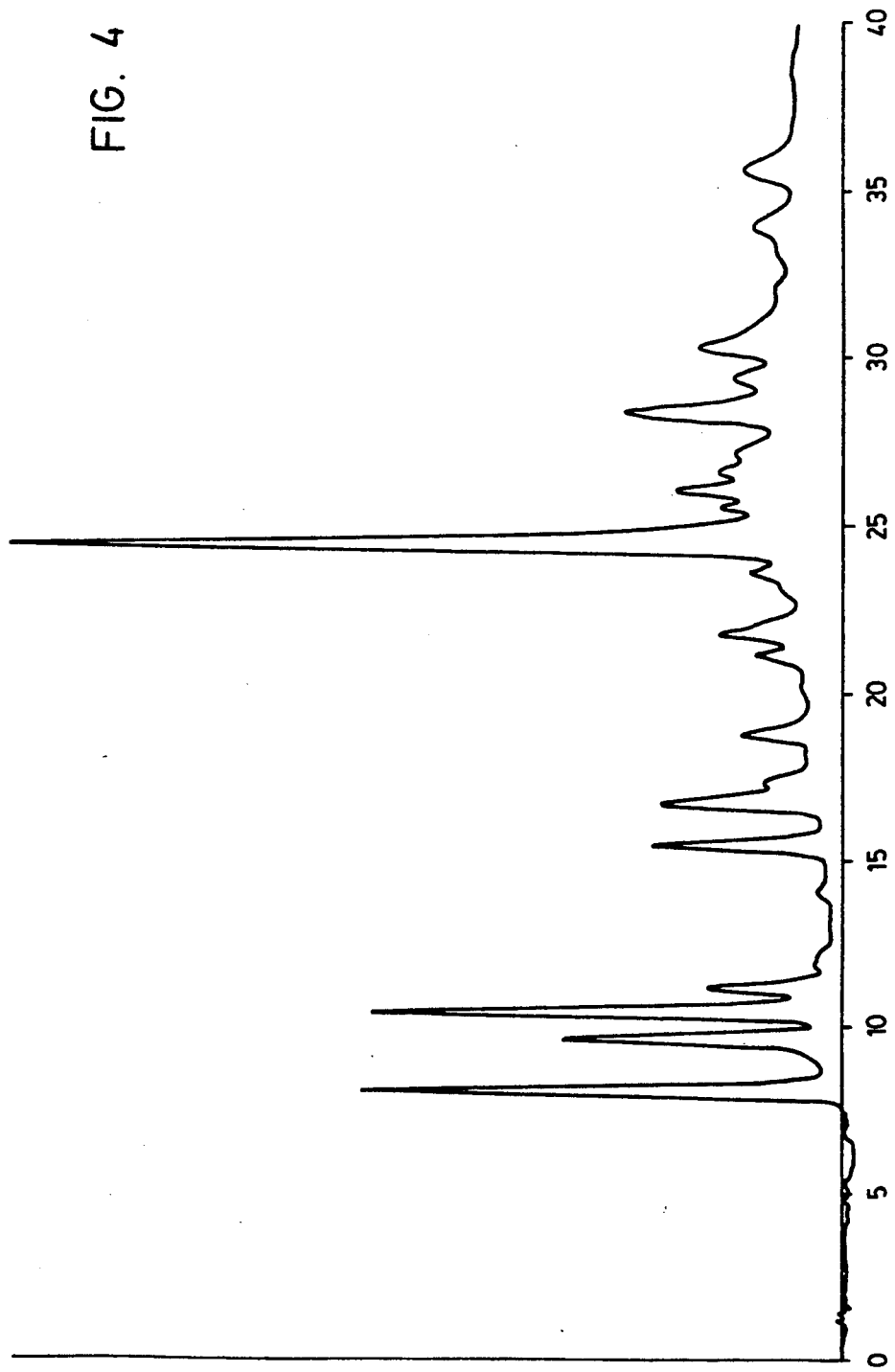
Figure 5:
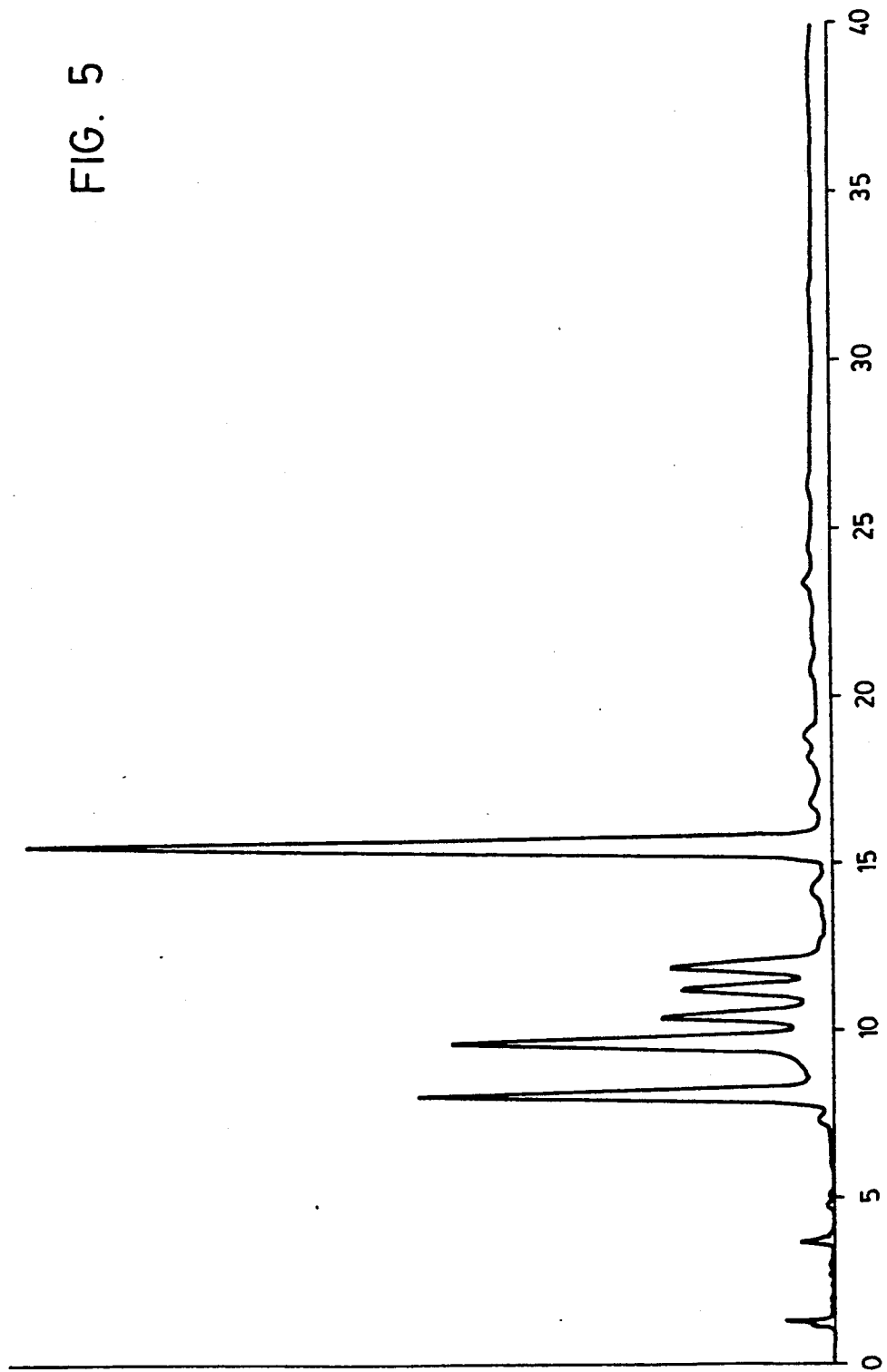
Figure 6:
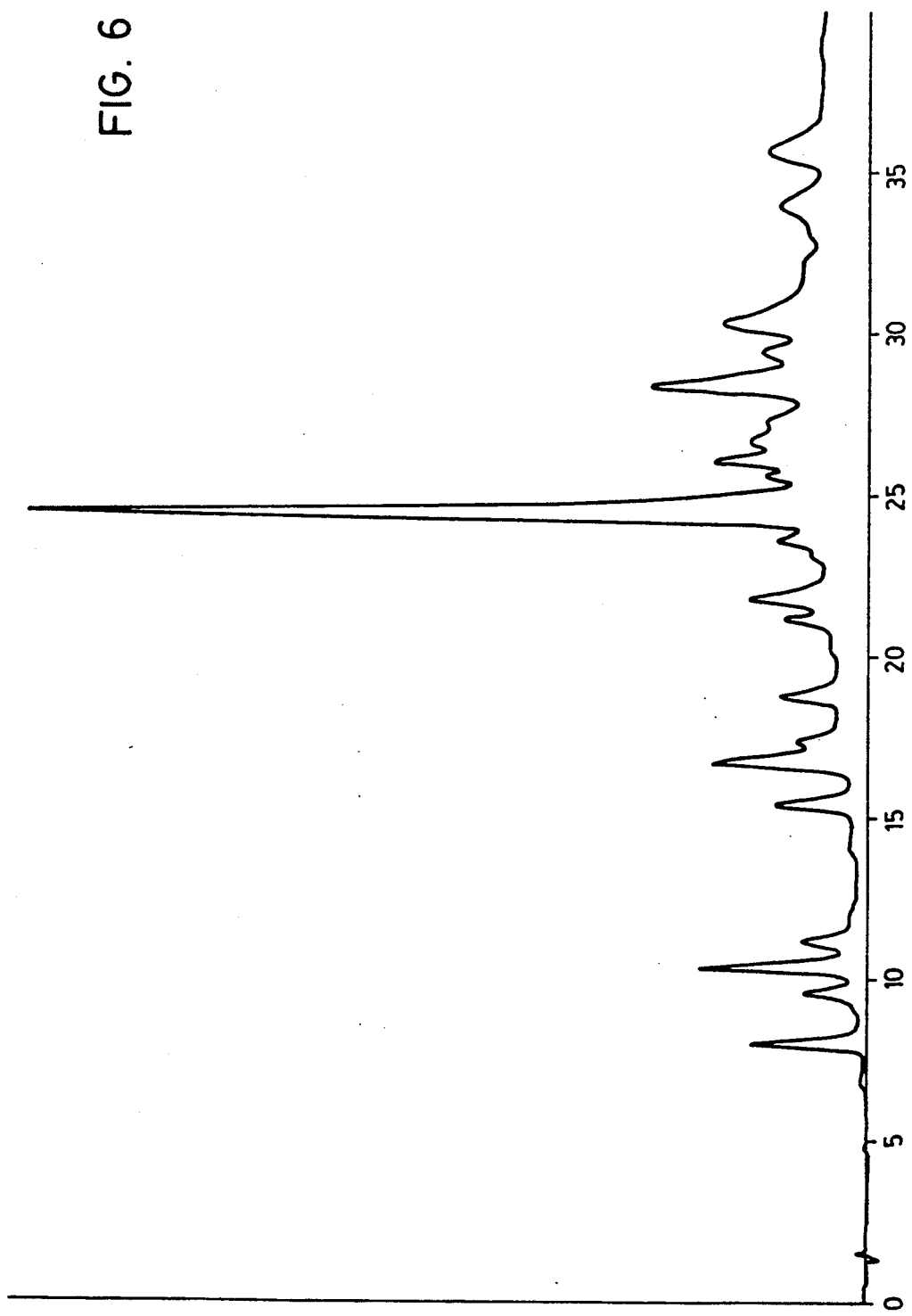
Figure 7:
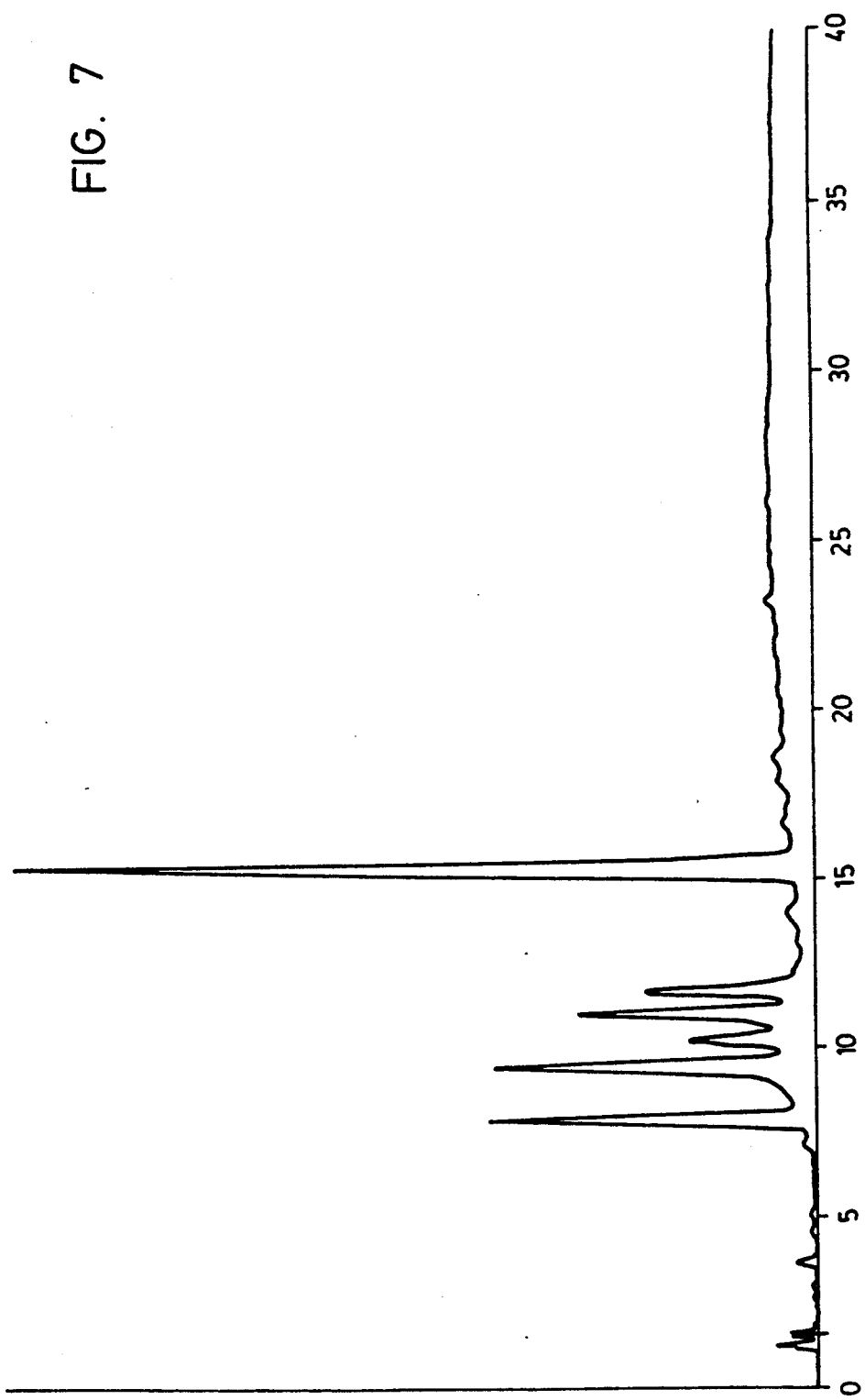
Figure 8:
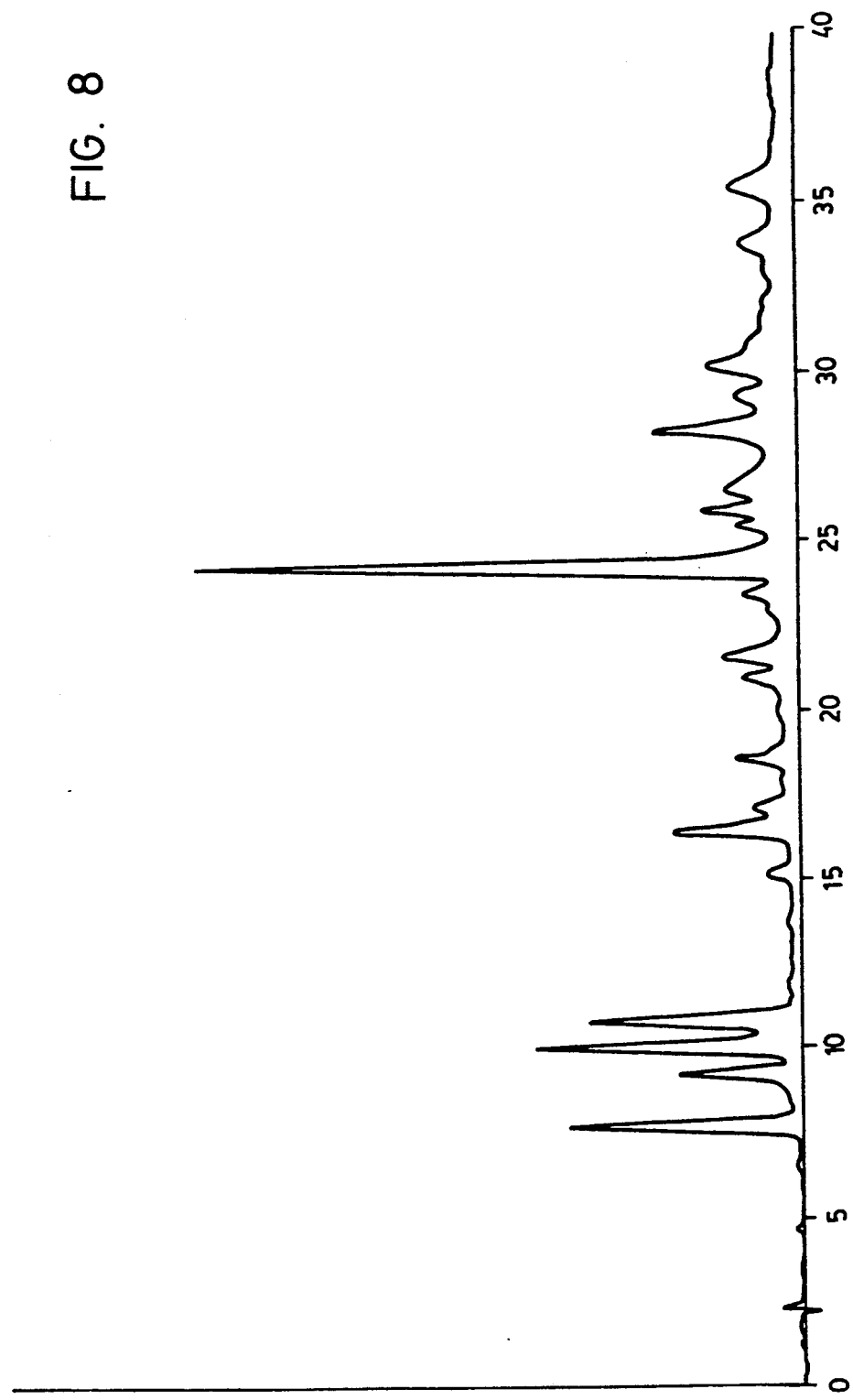
Figure 9:
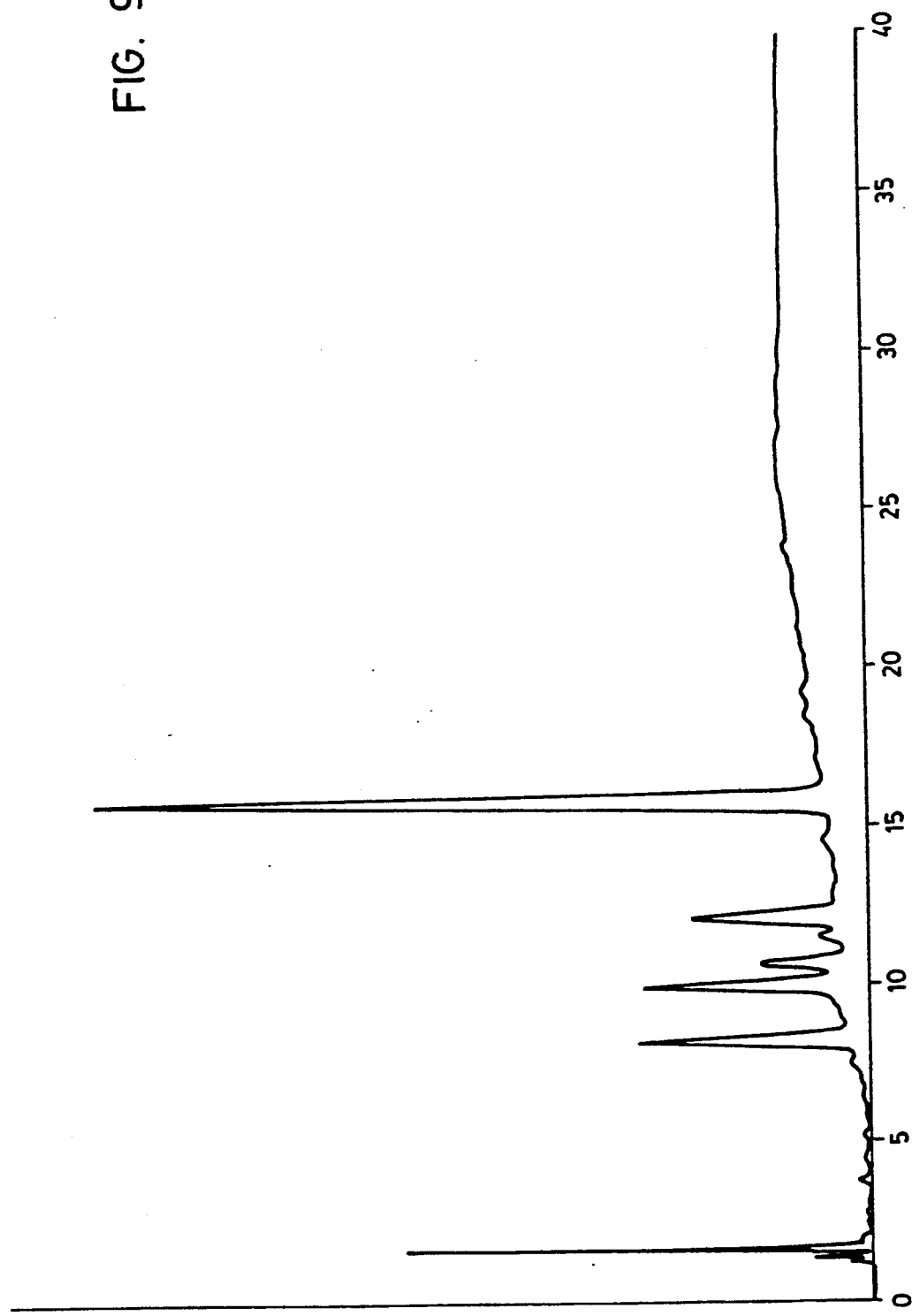
Figure 10:
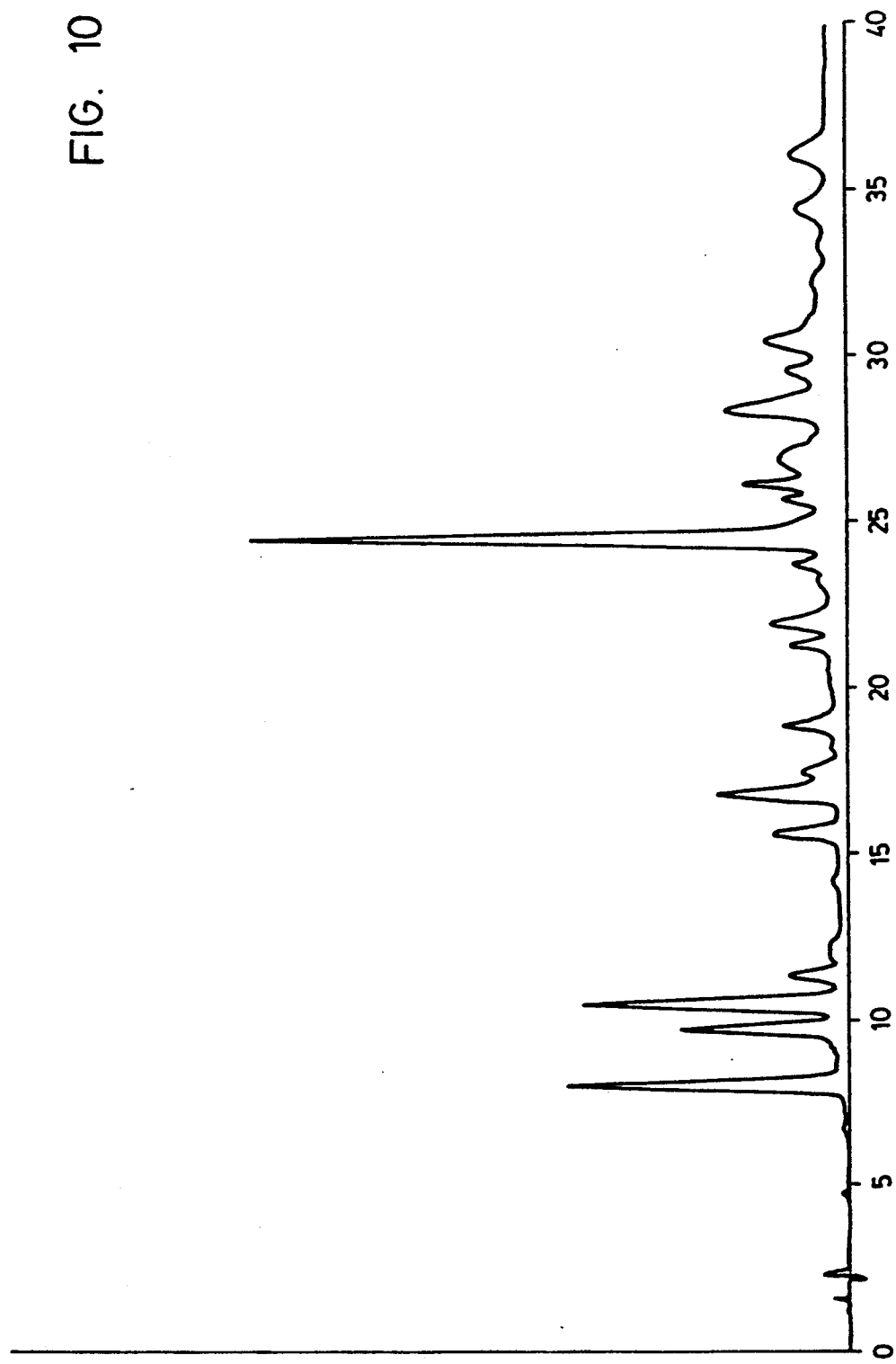

These chromatograms relate to the starting technical grade dicofol (FIG. 2); to the purified dicofol of Example 1 (FIG. 3), of Example 2 (FIG. 5), of Example 3 (FIG. 7) or of Example 4 (FIG. 9); and to the distillation residue of Example 1 (FIG. 4), of Example 2 (FIG. 6), of Example 3 (FIG. 8) or of Example 4 (FIG. 10).

Figure 2:
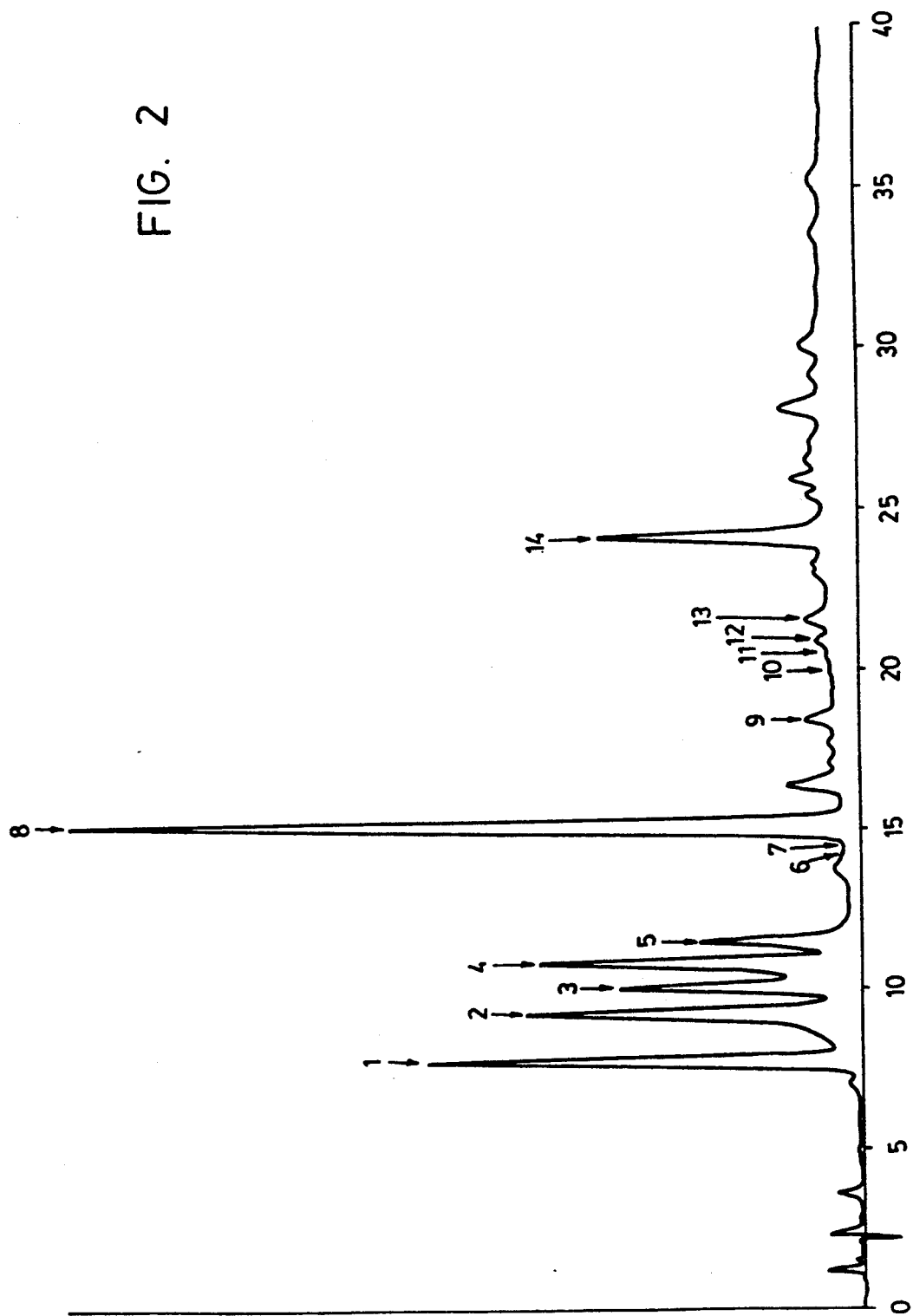
FIGS. 2 to 10 are chromatograms obtained in a high pressure liquid chromatography equipment (HPLC); the retention times in minutes are given in abscissae.

In FIG. 2, reference numbers are given to particular plaks. The corelation between the reference number and the product corresponding to the plak is as follows:

| Reference n° | Product |
| --- | --- |
| 1 | o,p'-DCBF |
| 2 | o,p'-DCBZ |
| 3 | p,p'-DCBF |
| 4 | p,p'-DCBZ |
| 5 | o,p'-dicofol |
| 6 | p,p'-DDD |
| 7 | o,p'-DDD |
| 8 | p,p'-dicofol |
| 9 | o,p'-DDE |
| 10 | p,p'-DDT |
| 11 | o,p'-DDT |
| 12 | p,p'-DDE |
| 13 | o,p'-ClDDT |
| 14 | p,p'-ClDDT |

EXAMPLE 1

Ethylene Glycol Monomethyl Ether (EMMEG) and Water System with n-decane.

Figure 1:
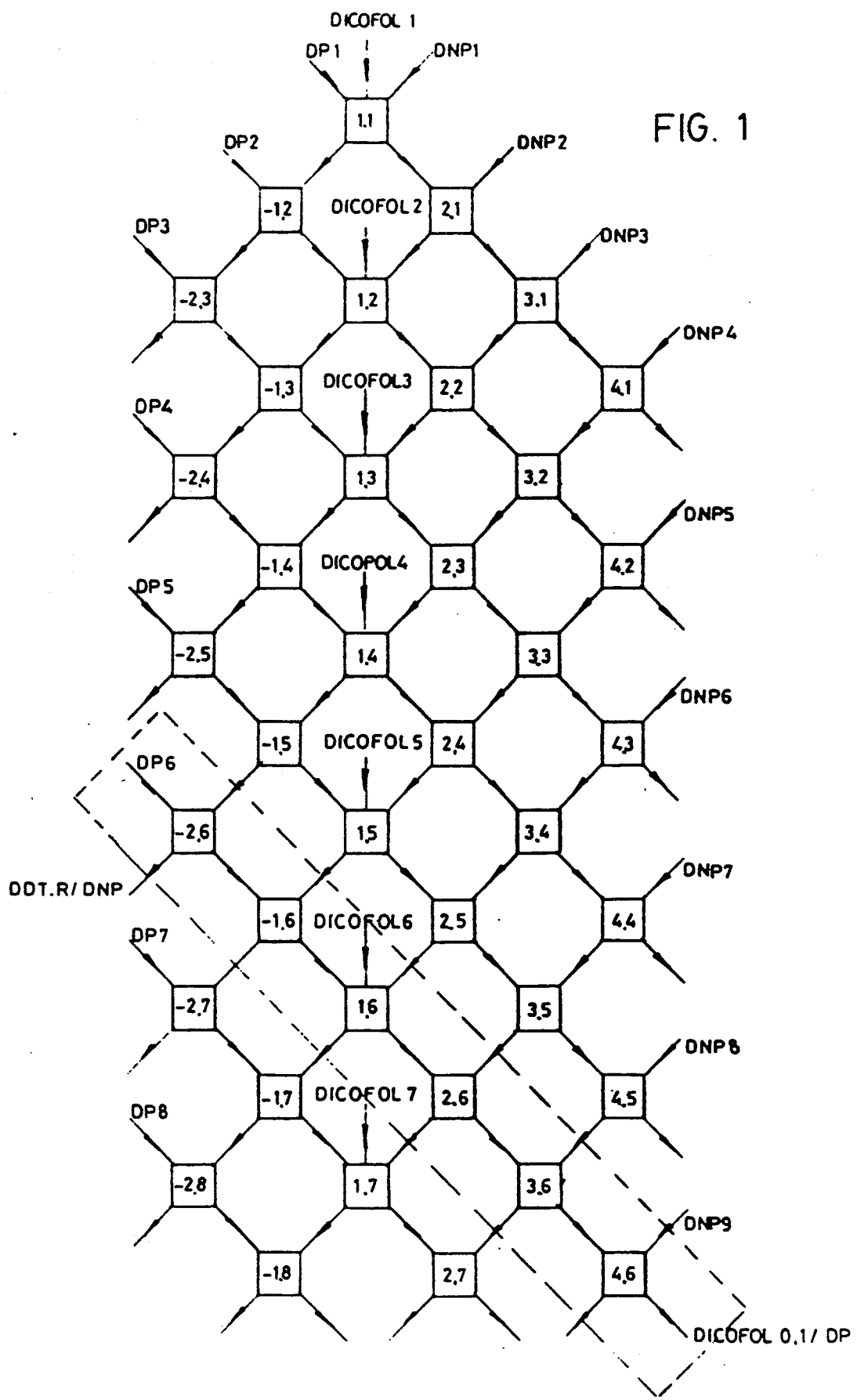
FIG. 1 a scheme of the liquid-liquid extraction process followed in the tests of the invention, in which PS means "polar solvent" and NPS means "non polar solvent"; in each square the FIGURE to the right is the serial number and the FIGURE to the left is the step number which, when preceded by the sign—means recovery and otherwise extraction.

10.0 g of technical grade dicofol, the composition of which determined by HPLC (see chromatogram of FIG. 2) is given in Table 1, were dissolved in a mixture of 21.0 g of ethylene glycol monomethyl ether and 5.0 g of water (PS1) and extracted in a separating funnel with 26.7 g of n-decane (NPS1). After allowing to rest, the separated phases were decanted and each of them was extracted with the complementary solvent, i.e. the more dense ethylene glycol monomethyl ether-water-dicofol phase was extracted with a further 26.7 g of n-decane (NPS2) and the n-decane phase was extracted with a further 21.0 g of ethylene glycol monomethyl ether and 5.0 g of water, mixed together and so on, following the scheme of FIG. 1, with the corresponding additions of 10.0 g portions of dicofol. The test was conducted at room temperature (20° C.).

Table 1. Results (wt %) of the simulation tests of continuous extraction in a counterflow column with the ethylene glycol monomethyl ether-water system and n-decane system.

TABLE I

|  | STARTING DICOFOL | | DICOFOL OBTAINED | | RESIDUE | DICOFOL USP 4705902 | |
| --- | --- | --- | --- | --- | --- | --- | --- |
|  | comp. | DDT.R | comp. | DDT.R | comp. | comp. | DDT.R |
| p,p'-dicofol | 70.5 |  | 79.6 |  | 25.7 | 79.8 |  |
| o,p'-dicofol | 14.7 |  | 16.7 |  | 4.5 | 16.6 |  |
| p,p'-DCBF | 0.4 |  | 0.09 |  | 1.2 | 0.13 |  |
| o,p'-DCBF | 0.4 |  | 0.24 |  | 1.7 | 0.26 |  |
| p,p'-DCBF | 0.7 |  | 0.05 |  | 0.5 | 0.06 |  |
| o,p'-DCBZ | 1.3 |  | 1.11 |  | 1.7 | 0.94 |  |
| p,p'-DDD | <0.01 | <0.01 | <0.01 | <0.01 | <0.1 | <0.01 | <0.01 |
| o,p'-DDD | <0.01 | <0.01 | <0.01 | <0.01 | <0.1 | <0.01 | <0.01 |
| p,p'-DDE | 0.03 | 0.03 | <0.01 | <0.01 | 0.2 | <0.01 | <0.01 |
| o,p'-DDE | 0.10 | 0.10 | 0.01 | 0.01 | 0.4 | 0.01 | 0.01 |
| p,p'-DDT | <0.01 | <0.01 | <0.01 | <0.01 | <0.1 | <0.01 | <0.01 |
| o,p'-DDT | <0.01 | <0.01 | <0.01 | <0.01 | <0.1 | <0.01 | <0.01 |
| p,p'-ClDDT | 3.5 | 3.5 | 0.03 | 0.03 | 28.0 | 0.11 | 0.11 |
| o,p'-ClDDT | 0.6 | 0.6 | <0.01 | <0.01 | 3.7 | 0.01 | 0.01 |
| unidentified | 7.8 | ? | 2.14 | <0.01 | 30.4 | 2.08 | <0.01 |
| R, dicofol, % |  |  | 95.6 |  |  | 97.4 |  |

The extracted dicofol containing less than 0.1 wt % of DDT.R was obtained in five extraction steps and a yield of 95.6% with two recovery steps, the system becoming stabilised in the 6th series.

By reduced pressure (10 mm Hg) distillation of the ethylene glycol monomethyl ether and water from the polar phase, the purified dicofol was recovered. The composition of the latter, determined by HPLC (see chromatogram of FIG. 3) may be seen in Table 1, compared with the product obtained in the same simulation test using the methanol-water system and n-heptane in the proportions described in U.S. Pat. No. 4,705,902, with five extraction and two recovery steps, with a 97.4% yield. The thus recovered solvent may be reused in the successive extraction operations.

The solvent, n-decane, may also be recovered by reduced pressure (10 mm Hg) distillation from the non-polar phase and may be recycled in the process.

The distillation residue is formed mainly by the non-polar impurities (DDT.R) contained in the starting dicofol. The approximate composition may be seen in Table 1 (see HPLC chromatogram of FIG. 4).

EXAMPLE 2.

Acetonitrile (AN) and Water System with n-decane.

10.0 g of technical grade dicofol, the composition of which determined by HPLC (see chromatogram of FIG. 2) is given in Table 2, were dissolved in a mixture of 27.3 g of acetonitrile and 5.2 g of water (PS1) and extracted in a separating funnel with 26.7 g of n-decane (NPS1). After resting, the separated phases were decanted and each of them was extracted with the complementary solvent, i.e. the denser acetonitrile-water-dicofol phase was extracted with a further 26.7 g of n-decane (NPS2) and the n-decane phase was extracted with a mixture of a further 27.3 g of acetonitrile and 5.2 g of water (PS2) and so on, following the scheme of FIG. 1, with the corresponding incorporation of 10.0 g portions of dicofol. The test was conducted at room temperature (23° C.).

Table 2. Results (in wt %) of the simulation tests of continuous extraction in counterflow column with the acetonitrile-water system and n-decane.

TABLE II

|  | STARTING DICOFOL | | DICOFOL OBTAINED | | RESIDUE | DICOFOL USP 4705902 | |
|---|---|---|---|---|---|---|---|
|  | comp. | DDT.R | comp. | DDT.R | comp. | comp. | DDT.R |
| p,p'-dicofol | 70.5 |  | 78.5 |  | 13.5 | 79.8 |  |
| o,p'-dicofol | 14.7 |  | 16.9 |  | 2.2 | 16.6 |  |
| p,p'-DCBF | 0.4 |  | 0.25 |  | 0.5 | 0.13 |  |
| o,p'-DCBF | 0.4 |  | 0.38 |  | 0.2 | 0.26 |  |
| p,p'-DCBZ | 0.7 |  | 0.30 |  | 0.3 | 0.06 |  |
| o,p'-DCBZ | 1.3 |  | 1.39 |  | 0.4 | 0.94 |  |
| p,p'-DDD | <0.01 | <0.01 | <0.01 | <0.01 | <0.1 | <0.01 | <0.01 |
| o,p'-DDD | <0.01 | <0.01 | <0.01 | <0.01 | <0.1 | <0.01 | <0.01 |
| p,p'-DDE | 0.03 | 0.03 | <0.01 | <0.01 | 0.2 | <0.01 | <0.01 |
| o,p'-DDE | 0.10 | 0.10 | 0.01 | 0.01 | <0.5 | 0.01 | 0.01 |
| p,p'-DDT | <0.01 | <0.01 | <0.01 | <0.01 | <0.1 | <0.01 | <0.01 |
| o,p'-DDT | <0.01 | <0.01 | <0.01 | <0.01 | 0.1 | <0.01 | <0.01 |
| p,p'-ClDDT | 3.5 | 3.5 | 0.04 | 0.04 | 35.6 | 0.11 | 0.11 |
| o,p'-ClDDT | 0.6 | 0.6 | <0.01 | <0.01 | 4.5 | 0.01 | 0.01 |
| unidentified | 7.8 | ? | 2.21 |  | 42.1 | 2.08 |  |
| R, dicofol, % |  |  | 98.2 |  |  | 97.4 |  |

5 extraction steps and 2 recovery steps are sufficient to obtain dicofol, the composition of which, determined by HPLC (see chromatogram in FIG. 5) appearing in Table 2, gives a DDT.R content of less than 0.1 wt % and a dicofol (1,1-bis(chlorophenyl-2,2,2-trichloroethanol) yield of 98.2%. Stabilisation was attained in the 6th series.

Dicofol with DDT.R content of less than 0.1 wt % is obtained as a residue in the vacuum distillation (10 mmHg) of the polar phase solvent, acetonitrile-water, which has proved to be reusable repeatedly in successive extractions.

These results are compared in the same Table with those obtained in the same simulation test using the methanol-water system and n-heptane, in the amounts taught in U.S. Pat. No. 4,705,902, with 5 extraction steps and 2 recovery steps, with a 97.4% yield.

Likewise, the distillation of the non polar phase, also at reduced pressure (10 mm Hg), allows the solvent, n-decane, to be recovered and reused repeatedly. The residue from this distillation is formed preferably by the nonpolar impurities (DDT.R) contained in the starting technical grade dicofol. The approximate composition may be seen in the Table (see HPLC chromatogram of FIG. 6). EXAMPLE 3. Dimethyl sulfoxide (DMSO) and water system with n-decane.

10.0 g of technical grade dicofol, the composition of which, determined by HPLC (See chromatogram of FIG. 2), appears in Table 3, were dissolved in a mixture of 21.0 g of dimethyl sulfoxide and 2.5 g of water (DP1) and were extracted in a separating funnel with 26.7 g of n-decane (NPS1). After being allowed to rest, the separated phases were decanted and each of them was extracted with the complementary solvent, that is, the denser dimethyl sulfoxide-water-dicofol phase was extracted with a further 26.7 g of n-decane (NPS2) and the n-decane phase was extracted with a mixture of a further 21.0 g of dimethyl sulfoxide and 2.5 g of water and so on, following the scheme of FIG. 1, with the corresponding incorporation of 10.0 g portions of dicofol. The test was performed at 55° C.

Table 3. Results (in wt %) of the simulation tests of continuous extraction in a counterflow column with the ethylene glycol monomethyl ether-water system and n-decane.

TABLE 3

|  | STARTING DICOFOL | | DICOFOL OBTAINED | | RESIDUE | DICOFOL USP 4705902 | |
|---|---|---|---|---|---|---|---|
|  | comp. | DDT.R | comp. | DDT.R | comp. | comp. | DDT.R |
| p,p'-dicofol | 70.5 |  | 79.4 |  | 7.7 | 79.8 |  |
| o,p'-dicofol | 14.7 |  | 16.2 |  | 2.5 | 16.6 |  |
| p,p'-DCBF | 0.4 |  | 0.20 |  | 1.4 | 0.13 |  |
| o,p'-DCBF | 0.4 |  | 0.32 |  | 0.7 | 0.26 |  |
| p,p'-DCBF | 0.7 |  | 0.51 |  | 1.6 | 0.06 |  |
| o,p'-DCBZ | 1.3 |  | 1.24 |  | 1.5 | 0.94 |  |
| p,p'-DDD | <0.01 | <0.01 | <0.01 | <0.01 | <0.1 | <0.01 | <0.01 |
| o,p'-DDD | <0.01 | <0.01 | <0.01 | <0.01 | <0.1 | <0.01 | <0.01 |
| p,p'-DDE | 0.03 | 0.03 | <0.01 | <0.01 | 0.3 | <0.01 | <0.01 |
| o,p'-DDE | 0.10 | 0.10 | 0.01 | 0.01 | 0.5 | 0.01 | 0.01 |
| p,p'-DDT | <0.01 | <0.01 | <0.01 | <0.01 | <0.1 | <0.01 | <0.01 |

TABLE 3-continued

| | STARTING DICOFOL | | DICOFOL OBTAINED | | RESIDUE | DICOFOL USP 4705902 | |
|---|---|---|---|---|---|---|---|
| | comp. | DDT.R | comp. | DDT.R | comp. | comp. | DDT.R |
| o,p'-DDT | <0.01 | <0.01 | <0.01 | <0.01 | <0.1 | <0.01 | <0.01 |
| p,p'-ClDDT | 3.5 | 3.5 | 0.07 | 0.07 | 35.1 | 0.11 | 0.11 |
| o,p'-ClDDT | 0.6 | 0.6 | <0.01 | <0.01 | 4.6 | 0.01 | 0.01 |
| unidentified | 7.8 | ? | 2.05 | <0.01 | 44.1 | 2.08 | <0.01 |
| R, dicofol, % | | | 98.8 | | | 97.4 | |

The extracted dicofol containing less than 0.1 (wt/%) of DDT.R was obtained with five extraction steps with a 98.8% yield, with one recovery step, the system being stabilised in the 6th series.

The purified dicofol was recovered by addition of water to the dimethyl sulfoxide-water-dicofol phase, extraction with carbon tetrachloride, washing and distillation. The composition, determined by HPLC (see chromatogram of FIG. 7), may be seen in Table 3 where these results are compared with those obtained in the same simulation test using the methanol-water system and n-heptane, with the rates described in U.S. Pat. No. 4,705,902, with five extraction steps and two recovery steps, with a 97.4% yield. Both the dimethyl sulfoxide (recovered by rectification) and the carbon tetrachloride, may be reused in successive extraction operations.

The solvent, n-decane, which may be recycled in the process, was also recovered by low pressure (10 mmHg) distillation of the non-polar phase. The distillation residue was formed mainly by the non-polar impurities (DDT.R) contained in the starting dicofol. The approximate composition may be seen in Table 3 (See HPLC chromatogram of FIG. 8).

EXAMPLE 4

Hydroxyacetone (HA) and water system with n-decane.

10.0 g of technical grade dicofol, the composition of which determinated by HPLC (see chromatogram of FIG. 2) is given in Table 4, were dissolved in a mixture of 21.0 g of hydroxyacetone and 2.0 g of water (PS1) and extracted in a separating funnel with 26.7 g of n-decane (NPS1). After resting, the separated phases were decanted and each of them was extracted with the complementary solvent, i.e. the denser hydroxyacetone-water-dicofol phase was extracted with a further 26.7 g of n-decane (NPS2) and the n-decane phase was extracted with a mixture of a further 21.0 g of hydroxyacetone and 2.0 g of water (PS2) and so on, following the scheme of FIG. 1, with the corresponding incorporation of 10.0 g portions of dicofol. The test was conducted at room temperature (20° C.).

Table 4. Results (in wt %) of the simulation tests of continuous extraction in counterflow column with the hydroxyacetone-water system and n-decane.

TABLE 4

| | STARTING DICOFOL | | DICOFOL OBTAINED | | RESIDUE | DICOFOL USP 4705902 | |
|---|---|---|---|---|---|---|---|
| | comp. | DDT.R | comp. | DDT.R | comp. | comp. | DDT.R |
| p,p'-dicofol | 70.5 | | 79.7 | | 20.2 | 79.8 | |
| o,p'-dicofol | 14.7 | | 16.6 | | 1.0 | 16.6 | |
| p,p'-DCBF | 0.4 | | 0.12 | | 1.2 | 0.13 | |
| o,p'-DCBF | 0.4 | | 0.28 | | 0.9 | 0.26 | |
| p,p'-DCBF | 0.7 | | 0.06 | | 0.4 | 0.06 | |
| o,p'-DCBZ | 1.3 | | 1.08 | | 1.9 | 0.94 | |
| p,p'-DDD | <0.01 | <0.01 | <0.01 | <0.01 | <0.1 | <0.01 | <0.01 |
| o,p'-DDD | <0.01 | <0.01 | <0.01 | <0.01 | <0.1 | <0.01 | <0.01 |
| p,p'-DDE | 0.03 | 0.03 | <0.01 | <0.01 | 0.3 | <0.01 | <0.01 |
| o,p'-DDE | 0.10 | 0.10 | 0.01 | 0.01 | 0.5 | 0.01 | 0.01 |
| p,p'-DDT | <0.01 | <0.01 | <0.01 | <0.01 | <0.1 | <0.01 | <0.01 |
| o,p'-DDT | <0.01 | <0.01 | <0.01 | <0.01 | <0.1 | <0.01 | <0.01 |
| p,p'-ClDDT | 3.5 | 3.5 | 0.02 | 0.02 | 32.7 | 0.11 | 0.11 |
| o,p'-ClDDT | 0.6 | 0.6 | 0.01 | 0.01 | 4.5 | 0.01 | 0.01 |
| unidentified | 7.8 | ? | 2.12 | <0.01 | 35.6 | 2.08 | <0.01 |
| R, dicofol, % | | | 97.6 | | | 97.4 | |

5 extraction steps and 2 recovery steps are sufficient to obtain dicofol, the composition of which, determined by HPLC (see chromatogram in FIG. 9) and appearing in Table 4, gives a DDT.R content of less than 0.1 wt % and a dicofol (1,1-bis(chlorophenyl-2,2,2-trichloroethanol) yield of 97.6%. Stabilisation was attained in the 6 th series.

Dicofol with DDT.R content of less than 0.1 wt % is obtained as a residue in the reduced pressure distillation (10 mmHg) of the polar phase solvent, hydroxyacetone-water, which has proved to be reusable repeatedly in successive extractions.

These results are compared in the same Table with those obtained in the same simulation test using the methanol-water system and n-heptane, in the amounts taught in U.S. Pat. No. 4,705,902, with 5 extraction steps and 2 recovery steps, with a 97.4% yield.

Likewise, the distillation of the non polar phase, also at reduced pressure (10 mmHg), allows the solvent, n-decane, to be recovered and reused repeatedly. The residue from this distillation is formed preferably by the non polar impurities (DDT.R) contained in the starting technical grade dicofol. The approximate composition may be seen in the Table 4 (see HPLC chromatogram of FIG. 10).

What we claim is:

1. A method for purifying technical grade, 1,1-bis-(chlorophenyl)-2,2,2-trichloroethanol with reduced amounts of DDT related impurities comprising the following steps: a) dissolving the 1,1-bis(chlorophenyl)-2,2,2-trichloroethanol in a polar solvent formed by a mixture of water and a first compound comprising ethylene glycol monomethyl ether, acetonitrile, hydroxyacetone or dimethyl sulfoxide, the water content in the solvent being at the most 25% by weight, yielding a solution in which the 1,1-bis(chlorophenyl)-2,2,2-trichloroethanol concentration lies between 5 and 35 wt %; b) extracting this solution with n-decane to provide an n-decane phase and a polar phase; c) separating the resulting phases; d) recovering the 1,1-bis(chlorophenyl)-2,2,2-trichloroethanol extracted by the n-decane by reextraction of the n-decane phase with mixtures of said first compound and water; e) recovering a purified 1,1-bis(chlorophenyl)-2,2,2-trichloroethanol from the polar phase.

2. A method according to claim 1, wherein the extraction is continuous.

3. A method according to claim 1, wherein the resulting phases are separated by decantation.

4. A method according to claim 1, wherein, when the first compound is ethylene glycol monomethyl ether, acetonitrile or hydroxyacetone, the 1,1-bis(chlorophenyl)-2,2,2-trichloroethanol is recovered by distillation of the polar phase at reduced pressure, whereby the mixture of water with ethylene glycol monomethyl ether, with acetonitrile or with hydroxyacetone is recovered and recycled in the process and the purified 1,1-bis(chlorophenyl)-2,2,2-trichloroethanol is obtained as a residue.

5. A method according to claim 1, wherein when the first compound is dimethyl sulfoxide, the 1,1-bis(chlorophenyl)-2,2,2-trichloroethanol is recovered by, diluting the dimethyl sulfoxide with water, extracting with a second solvent, separating the liquid phases formed, removing said second solvent by reduced pressure distillation and obtaining the purified 1,1-bis(chlorophenyl)-2,2,2-trichloroethanol as residue.

6. A method according to claim 5, wherein the dimethyl sulfoxide is recovered from one of the liquid phases formed by distillation and is recycled to step (a).

7. A method according to claim 5, wherein said second solvent is carbon tetrachloride.

8. A method according to claim 1, wherein the DDT-related impurity content in the end product is less than 0.1 wt %.

9. A method according to claim 1, wherein the method is conducted at temperatures ranging from 0° to 100° C.

10. A method according to claim 5, wherein the method is continuous.

11. A method according to claim 10, wherein the method is conducted in at least one countercurrent column.

12. A method according to claim 11, wherein the method is conducted in decanting mixers.

* * * * *

UNITED STATES PATENT AND TRADEMARK OFFICE
CERTIFICATE OF CORRECTION

PATENT NO. : 5,075,512

DATED : December 24, 1991

INVENTOR(S) : Jaime P. Adrubau and Jaume Castella Sola

It is certified that error appears in the above-identified patent and that said Letters Patent is hereby corrected as shown below:

Column 2, lines 22 and 23, "1-(4-chlorophenyl)-2,2-dichloroethylene (o,p'-DDE)" should read --1-(4-chlorophenyl)-1-(2-chlorophenyl)-2,2-dichloroethylene (o,p'-DDE)--.

Column 3, lines 47 and 48 "2,4'-dichlorpbenzophenone" should read --2,4'-dichlorobenzophenone--.

Column 8, lines 15 and 16, "EXAMPLE 3. Dimethyl sulfoxide (DMSO) and water system with n-decane." is a title and should be separate from the adjacent text.

Column 8, line 53, "ethylene glycol monomethyl ether-water" should read --dimethyl sulfoxide-water--.

Signed and Sealed this

Seventeenth Day of August, 1993

Attest:

BRUCE LEHMAN

*Attesting Officer*                    *Commissioner of Patents and Trademarks*